(12) United States Patent
Dyballa et al.

(10) Patent No.: US 10,167,244 B2
(45) Date of Patent: Jan. 1, 2019

(54) METHOD FOR HYDROFORMYLATING CYCLOOCTADIENE USING 2-(ANTHRACEN-9-YLOXY)-4,4,5,5-TETRAMETHYL-1,3,2-DIOXAPHOSPHOLANE

(71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Dieter Hess, Marl (DE); Detlef Selent, Rostock (DE); Armin Börner, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/939,373

(22) Filed: Mar. 29, 2018

(65) Prior Publication Data

US 2018/0290956 A1  Oct. 11, 2018

(30) Foreign Application Priority Data

Apr. 11, 2017 (EP) .................................... 17165992

(51) Int. Cl.
  *C07C 45/50*  (2006.01)
  *B01J 31/00*  (2006.01)
  *B01J 31/18*  (2006.01)

(52) U.S. Cl.
  CPC ............. *C07C 45/50* (2013.01); *B01J 31/185* (2013.01); *B01J 2231/321* (2013.01); *B01J 2531/822* (2013.01)

(58) Field of Classification Search
  CPC ................................ C07C 45/50; B01L 31/185
  See application file for complete search history.

(56) References Cited

U.S. PATENT DOCUMENTS

| 5,202,297 A | 4/1993 | Lori et al. |
| 9,359,278 B2 | 6/2016 | Christiansen et al. |
| 2016/0159718 A1 | 6/2016 | Dyballa et al. |
| 2016/0159837 A1 | 6/2016 | Dyballa et al. |

FOREIGN PATENT DOCUMENTS

| EP | 0 472 071 A1 | 2/1992 |
| EP | 3 029 013 A1 | 6/2016 |

OTHER PUBLICATIONS

U.S. Appl. No. 15/939,395, filed Mar. 29, 2018, Dyballa, et al.
European Search Report for EP17165992, dated May 23, 2017 (7 Pgs. in German).
Franke, R.et al. Applied Hydroformylation. Chemical Reviews. 2012. pp. 5675-5732.
Trzeciak, A. M. et al. Rhodium Complex Catalyzed Hydroformylation Reactions of Linear and Cyclic Mono- and Diolefins, Journal of Organometallic Chemistry, 479, 1994. pp. 213-216.
Salvadori, P et al. Selective Hydroformylation of Cyclodienes to Cycloalkenecarboxaldehydes Using Catalysts Derived Directly from Rh Vapour and Cyclodienes. Journal of Organometallic Chemistry, 258, 1983. pp. 351-355.
Maringgele, W. et al. Umsetzung Von Lithiiertem 2-Hydroxybiphenyl Bzw. 2'-Hydroxy-Mterphenyl Mit Halogenverbindungen Von Silicium Und Germanium, Phosphor Und Arsen [Implementation of Lithiated 2-Hydroxybiphenyl BZW. 2'-Hydroxy-M-Terphenyl With Halogen Compounds of Silicium and Germanium, Phosphorus and Arsen]. Phosphorus, Sulfur and Silicon. 1994. vol. 90, pp. 235-241 (in German with English machine translation).

*Primary Examiner* — Sikarl A Witherspoon
(74) *Attorney, Agent, or Firm* — Smith, Gambrell & Russell, LLP

(57) ABSTRACT

A catalytic method for hydroformylating a cyclooctadiene substrate involving forming a reaction mixture that includes the cyclooctadiene and a precursor of or a transitional metal ligand complex where the ligand has structure (1):

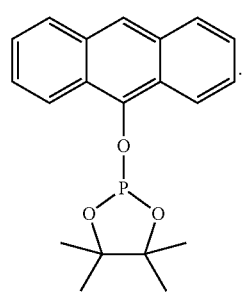

(1)

$H_2$ and CO are fed into the reaction mixture and the mixture is heated to convert the cyclooctadiene into an aldehyde. A preferred ligand is 2-(anthracen-9-yloxy)-4,4,5,5-tetramethyl-1,3,2-dioxaphospholane.

5 Claims, No Drawings

METHOD FOR HYDROFORMYLATING CYCLOOCTADIENE USING 2-(ANTHRACEN-9-YLOXY)-4,4,5,5-TETRAMETHYL-1,3,2-DIOXAPHOSPHOLANE

The invention relates to a method for hydroformylating cyclooctadiene (COD) using 2-(anthracen-9-yloxy)-4,4,5,5-tetramethyl-1,3,2-dioxaphospholane.

Phosphorus-containing compounds, as ligands, play a crucial role in a multitude of reactions. Said compounds include phosphite ligands, i.e., compounds comprising P—O bonds, used in hydrogenation, hydrocyanation and especially hydroformylation.

The reactions between olefin compounds, carbon monoxide and hydrogen in the presence of a catalyst to give the aldehydes with one carbon atom more are known as hydroformylation or the oxo process. In these reactions, compounds of the transition metals of group VIII of the Periodic Table of the Elements are frequently employed as catalysts. Known ligands are, for example, compounds from the classes of the phosphines, phosphites and phosphorites, each with trivalent phosphorus PIII. A good overview of the status of hydroformylation of olefins is found in R. Franke, D. Selent, A. Börner, "Applied Hydroformylation", Chem. Rev., 2012, DOI:10.1021/cr3001803.

The object of the invention is to provide a method for hydroformylating cyclooctadiene which affords good conversion of cyclooctadiene.

The object is achieved by the following method.

Method for hydroformylating cyclooctadiene, comprising the method steps of:

a) initially charging cyclooctadiene;
b) adding a complex comprising:
a metal atom selected from: Rh, Ru, Co, Ir, and
a ligand having the structure (1):

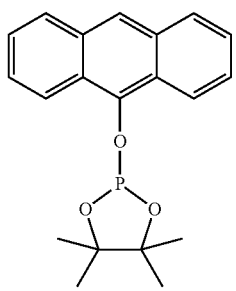

(1)

or adding a precursor complex comprising a metal atom selected from: Rh, Ru, Co, Ir, and a compound having the structure (1):

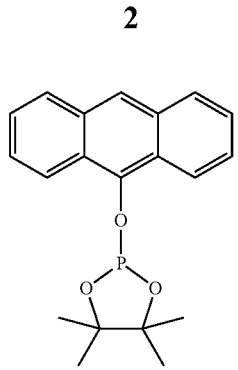

(1)

c) feeding in $H_2$ and CO,
d) heating the reaction mixture, wherein the cyclooctadiene is converted to an aldehyde.

Here, method steps a) to d) can be effected in any desired sequence.

In one variant of the method, the metal atom is Rh.

In one variant of the method, the precursor complex comprises cyclooctadiene.

In one variant of the method, the precursor complex is [(acac)Rh(COD)].

In this instance, "acac" is acetylacetonate anion and "COD" is cyclooctadiene.

In one variant of the method, the reaction mixture is heated to a temperature in the range of 50° C. to 70° C. in method step d).

The invention is elucidated in detail hereinafter by working examples.

Analysis

Chromatography

The preparative liquid chromatography separations via flash chromatography were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-film chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulfate tetrahydrate and 13.3 g of concentrated sulfuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme; "hard" method: start temperature of 50° C. for 1 min, heating rate: 15° C./min, end temperature of 290° C. for 8 min). Gas chromatography-mass spectrometry analyses (GCMS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature of 50° C. for 1 min, heating rate: 15° C./min, end temperature of 290° C. for 8 min; GCMS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the organic chemistry department of Johannes Gutenberg University Mainz on a Vario EL Cube from Foss-Heraeus, Hanau.

Mass Spectrometry

All electrospray ionization analyses (ESI+) were conducted on a QTof Ultima 3 from Waters Micromasses, Milford, Mass. EI mass spectra and the high-resolution EI spectra were analyzed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1 H and 13 C spectra were calibrated according to the residual content of undeuterated solvent using the NMR Solvent Data Chart from Cambridge Isotopes Laboratories, USA. Some of the 1 H and 13 C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not correspond to IUPAC nomenclature.

General Procedure Specifications

All preparative procedures were conducted applying the Schlenk technique with argon as protective gas. Toluene and tetrahydrofuran were purified using a Pure Solv MD-7 System and stored under argon before use. Triethylamine was distilled under argon from sodium ketyl before use. Phosphorus trichloride (Aldrich) was distilled under argon before use. All preparative procedures were effected in baked-out vessels. The recording of nuclear resonance spectra was effected on Bruker Avance 300 or Bruker Avance 400, gas chromatography analysis was effected on Agilent GC 7890A, elemental analysis was effected on Leco TruSpec CHNS and Varian ICP-OES 715, and ESI-TOF mass spectrometry was effected on Thermo Electron Finnigan MAT 95-XP and Agilent 6890 N/5973 instruments, semiautomatic column chromatography was effected on a Teledyne Isco Combiflash Rf+.

SYNTHESES a) (Anthracen-9-yloxy)dichlorophosphane (precursor)

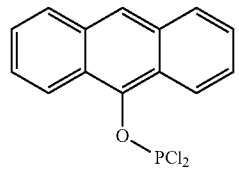

Added dropwise to a stirred solution of $PCl_3$ (5.16 g; 37.6 mmol) in THF (25 ml) at 10° C. within 90 min is a mixture of anthrone (2.03 g; 10.44 mmol) and triethylamine (2 ml) in THF (80 ml). After being left to stand overnight, the mixture is filtered, the filtrate is concentrated to dryness under reduced pressure and the residue obtained is taken up in toluene (50 ml). The mixture is filtered again, the solvent is removed under reduced pressure and the yellow residue is dried at 50° C./0.1 mbar. Subsequently, the solid obtained is stirred with hexane (30 ml) at room temperature overnight. The mixture is filtered and the filtercake is washed again with hexane (3 ×20 ml) and dried. Yield: 2.27 g (73%). $^{31}P$-NMR ($CD_2Cl_2$): 202.5 (s) ppm.

b) 2-(Anthracen-9-yloxy)-4,4,5,5-tetramethyl-1,3,2-dioxaphospholane (ligand 1)

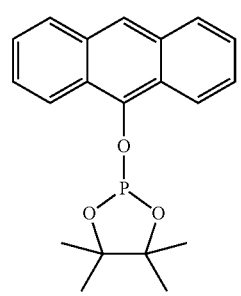

(1)

To a mixture of pinacol (0.426 g; 3.606 mmol), triethylamine (4.6 ml) and toluene (14 ml), stirred at 0° C., is added dropwise a solution of (anthracen-9-yloxy)dichlorophosphane (1.117 g; 3.787 mmol) in toluene (17 ml). The mixture is allowed to come to room temperature, stirred overnight and filtered through a G4 frit coated with silica gel. The filtrate is concentrated to dryness under vacuum and the remaining residue dried at 50° C./0.1 mbar for 5 h. Elemental analysis (calc. for $C_{20}H_{21}O_3P$=340.35 g/mol): C 70.35 (70.58); H 6.19 (6.22); P 8.97 (9.10)%, ESI-TOF/HRMS: m/e 341.13075 (M+H)+.

$^{31}P$-NMR ($CD_2Cl_2$): 145.3 (s) ppm.

$^{1}H$-NMR ($CD_2Cl_2$): 1.27 (s, 6H); 1.55 (s, 6H); 7.32-7.43 (m, 4H); 7.85 (d, $J_{HH}$=8.6 Hz, 2H); 8.09 (s, 1H); 8.27 (d, $J_{HH}$=8.6 Hz, 2H) ppm.

$^{13}C$-NMR ($CD_2Cl_2$): 24.9; 25.2; 86.5 (d, $J_{CP}$=7.5 Hz); 122.1; 123.0; 124.9; 125.6; 125.7; 128.1; 132.2; 144.1 (d, $J_{CP}$=6.2 Hz) ppm.

c) 4-(Anthracen-9-yloxy)-S-dinaphtho[2,1-d:1',2'-f][1,3,2]dioxaphosphepine (ligand 2)

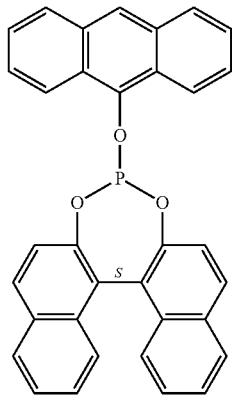

(2)

To a suspension of anthrone (0.447 g; 2.30 mmol) in THF (5 ml), stirred at −20° C., is added dropwise a 0.32M solution of n-butyllithium in heptane (7.2 ml; 2.30 mmol). The mixture is allowed to come to room temperature and a solution of 4-chloro-S-dinaphtho[2,1-d:1',2'-f][1,3,2]dioxaphosphepine (0.807 g; 2.30 mmol) in THF (6 ml) is then added dropwise with stirring. The mixture is stirred overnight and filtered. The volatile constituents of the filtrate are removed under reduced pressure, the resulting yellow solid is taken up in toluene (10 ml), filtered through a G4 frit coated with silica gel and the filtrate is concentrated under reduced pressure. The resulting solid is dried at 50° C./0.1 mbar for 3 h. The work-up by column chromatography (hexane/$CH_2Cl_2$, gradient hexane 100→0%; $R_f$=0.5 for a 1:1 mixture of the mobile phases) gives 0.55 g (1.08 mmol; 47%) of pure product. Elemental analysis (calc. for $C_{34}H_{21}O_3P$=508.511 g/mol): C 80.80 (80.31); H 3.89 (4.16); P 6.02 (6.09) %. ESI-TOF/HRMS: m/e 509.12979 (M+H)$^+$.

$^{31}$P-NMR ($CD_2Cl_2$): 149.7 (s) ppm.

$^1$H-NMR ($CD_2Cl_2$): 7.37-7.42 (m, 2H); 7.51-7.65 (m, 9H); 7.87 (d, $J_{HH}$=8.9 Hz, 1H); 8.02-8.14 (m, 6H); 8.40 (s, 1H); 8.57 (d, $J_{HH}$=8.9 Hz, 2H) ppm.

$^{13}$C-NMR ($CD_2Cl_2$): 122.1; 122.4; 123.0; 123.6; 123.8; 124.7; 125.0; 125.7; 126.1; 126.5; 127.0; 127.3; 128.6; 128.9; 130.6; 131.1; 131.9; 132.3; 132.6; 133.1; 133.4; 143.5 (d, $J_{CP}$=6.1 Hz); 147.4 (d, $J_{CP}$=2.7 Hz); 148.3 (d, $J_{CP}$=5.2 Hz) ppm.

d) 2-([1,1':3',1''-Terphenyl]-2'-yloxy)-4,4,5,5-tetramethyl-1,3,2-dioxaphospholane (ligand 3)

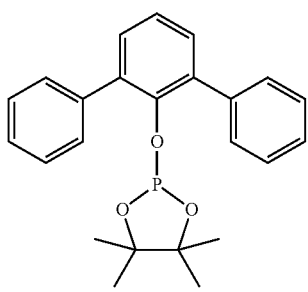

(3)

The required 2,6-diphenylphen-I-oxydichlorophosphine was prepared as described in W. Maringgele, A. Meller, *Phosphorus, Sulfur and Silicon* 1994, 90, 235-241.

To a solution of 2,6-diphenylphen-I-oxydichlorophosphine (1.048 g; 3.018 mmol) in toluene (18 ml), stirred at 0° C., is added dropwise a mixture of pinacol (0.3405 g; 2.881 mmol) and triethylamine (3.65 ml) in toluene (12 ml). The mixture is allowed to come to room temperature, stirred overnight and filtered. The filtrate is concentrated and the resulting residue is crystallized multiple times from hot heptane. Yield: 0.295 g (0.752 mmol; 26%). Elemental analysis (calc. for $C_{24}H_{25}O_3P$=392.41 g/mol): C 73.31 (73.45); H 6.42 (6.42); P 7.53 (7.89) %. ESI-TOF/HRMS: m/e 393.16143, (M+H)$^+$.

$^{31}$P-NMR ($CD_2Cl_2$): 142.9 (s) ppm.

$^1$H-NMR ($CD_2Cl_2$): 1.17 (s, 6H), 1.31 (s, 6H), 7.34-7.72 (m, 13H) ppm.

$^{13}$C-NMR ($CD_2Cl_2$) δ 147.4 (d, $J_{CP}$=6.5 Hz); 139.4; 136.6; 130.9; 130.8; 128.5; 127.6; 124.7; 85.3 (d, $J_{CP}$=8.0 Hz); 25.5; 24.8 ppm.

Hydroformylation

The hydroformylation reactions were conducted in a 200 ml autoclave equipped with pressure-retaining valve, gas flow meter, sparging stirrer and pressure pipette from Premex Reactor AG, Lengau, Switzerland. The toluene used as solvent was purified using a Pure Solv MD-7 System and stored under argon.

For the experiments, solutions of the precursor complex (=catalyst precursor) and the ligand were mixed in the autoclave under an argon atmosphere. [(acac)Rh(COD)] (Umicore, acac=acetylacetonate anion; COD=1,5-cyclooctadiene) was used as precursor complex. For experiments at a concentration of 100 ppm-m rhodium, 5 ml of a 4.32 millimolar solution was placed in the autoclave. Subsequently, the mass of ligand corresponding to a ratio L/Rh=5:1 was dissolved and mixed in 20 ml of toluene. Into a pressure-resistant pipette was filled: 2.69 g (24.86 mmol) of COD-1,5. The autoclave was brought to a pressure of 42 bar with synthesis gas (Linde; H2 (quality 5.0: CO (quality 4.7)=1:1) and heated to 60° C. After reaching the reaction temperature, the diolefin was compressed into the autoclave. The reaction was conducted at a constant pressure of 50 bar (closed-loop pressure controller from Bronkhorst, the Netherlands). After the reaction time had elapsed, the autoclave was cooled to room temperature, decompressed while stirring and purged with argon. 1 ml of each reaction mixture was removed immediately after the stirrer had been switched off, diluted with 5 ml of pentane and analyzed by gas chromatography: HP 5890 Series II plus, PONA, 50 m×0.2 mm×0.5 μm.

The results of the hydroformylation experiments are compiled in the following table. The conversion specified includes in this case both monoaldehydes and dialdehydes.

Standard experimental conditions: [Rh]=0.717×10$^{-4}$ M, Rh/ligand/COD-1,5=1:5:1151, solvent toluene.

TABLE 1

| Ligand | p [bar] | T [° C.] | t [h] | Conversion COD-1,5 [%] |
|---|---|---|---|---|
| 1* | 50 | 60 | 4 | 91 |
| 2 | 50 | 60 | 4 | 54 |
| 3 | 50 | 60 | 4 | 76 |

*method according to the invention

As the experimental results show, the object is achieved by the inventive method.

The invention claimed is:
1. A method for hydroformylating cyclooctadiene, comprising the method steps of:
   a) initially charging cyclooctadiene;
   b) adding a complex comprising:
   a metal atom selected from: Rh, Ru, Co, Ir, and
   a ligand having the structure (1):

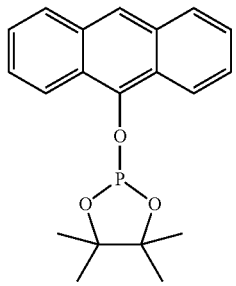

(1)

or
   adding a precursor complex comprising a metal atom selected from: Rh, Ru, Co, Ir, and a compound having the structure (1):

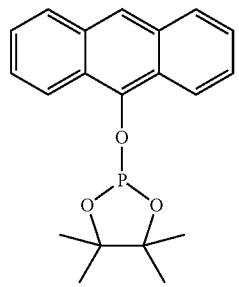

(1)

c) feeding in $H_2$ and CO,
   d) heating the reaction mixture, wherein the cyclooctadiene is converted to an aldehyde.

2. The method according to claim 1, wherein the metal atom is Rh.

3. The method according to claim 1, wherein the precursor complex comprises cyclooctadiene.

4. The method according to claim 1, wherein the precursor complex is [(acac)Rh(COD)].

5. The method according to claim 1, wherein the reaction mixture is heated to a temperature in the range of 50° C. to 70° C. in method step d).

* * * * *